(12) United States Patent
Koga

(10) Patent No.: US 8,746,282 B2
(45) Date of Patent: Jun. 10, 2014

(54) CHECK VALVE ASSEMBLY FOR ENDOSCOPE

(75) Inventor: Takehiko Koga, Kanagawa (JP)

(73) Assignee: Fujifilm Corporation, Tokyo (JP)

( * ) Notice: Subject to any disclaimer, the term of this patent is extended or adjusted under 35 U.S.C. 154(b) by 442 days.

(21) Appl. No.: 13/171,192

(22) Filed: Jun. 28, 2011

(65) Prior Publication Data

US 2012/0018011 A1     Jan. 26, 2012

(30) Foreign Application Priority Data

Jul. 22, 2010   (JP) .................................. 2010-164809

(51) Int. Cl.
*F16K 15/14*         (2006.01)
(52) U.S. Cl.
USPC ......................................................... 137/853
(58) Field of Classification Search
CPC ............ B65D 47/205; B65D 83/0055; B67D 1/0082; A61B 1/00068; A61B 1/12
USPC .......... 137/843, 844, 846, 848, 851, 852, 853
See application file for complete search history.

(56) References Cited

U.S. PATENT DOCUMENTS

| 3,231,149 | A | * | 1/1966 | Yuza | 222/324 |
| 3,342,208 | A | * | 9/1967 | Steffes | 137/516.11 |
| 3,417,775 | A | * | 12/1968 | Smith | 137/218 |
| 4,325,362 | A | * | 4/1982 | Ouchi et al. | 600/158 |
| 4,346,704 | A | * | 8/1982 | Kulle | 604/247 |
| 4,779,624 | A | * | 10/1988 | Yokoi | 600/439 |
| 5,033,647 | A | * | 7/1991 | Smith et al. | 222/94 |
| 5,133,336 | A | * | 7/1992 | Savitt et al. | 600/132 |
| 5,191,878 | A | * | 3/1993 | Iida et al. | 600/157 |
| 5,226,568 | A | * | 7/1993 | Newton et al. | 222/212 |
| 5,613,957 | A | * | 3/1997 | Py | 604/294 |
| 5,755,263 | A | * | 5/1998 | Jang | 137/853 |
| 5,836,484 | A | * | 11/1998 | Gerber | 222/494 |
| 5,891,014 | A | * | 4/1999 | Akiba | 600/158 |
| 6,254,579 | B1 | * | 7/2001 | Cogger et al. | 604/298 |

(Continued)

FOREIGN PATENT DOCUMENTS

JP      48-74324       9/1973
JP      2005-160772 A  6/2005

OTHER PUBLICATIONS

Japanese Office Action dated Oct. 30, 2013, with English translation.

*Primary Examiner* — John K Fristoe, Jr.
*Assistant Examiner* — Frederick D Soski
(74) *Attorney, Agent, or Firm* — McGinn IP Law Group, PLLC

(57) ABSTRACT

A check valve assembly includes a valve housing upstream of an endoscope. A tubular discharge nozzle unit is mounted in the valve housing, and supplied with fluid by a fluid supply source. The discharge nozzle unit includes a large diameter portion, a small diameter portion, formed on the large diameter portion on a distal side, and having a closed distal end nearer to the endoscope, and a fluid opening formed through a wall of the small diameter portion. An elastic tubular portion (sleeve) is contained in the valve housing, disposed around the small and large diameter portions, shaped tubularly with a substantially regular thickness, having an inner diameter which is smaller than an outer diameter of the small diameter portion in a normal state, for preventing the fluid from backflow into the fluid opening through the outer surface on a side downstream of the discharge nozzle unit.

14 Claims, 8 Drawing Sheets

(56) References Cited

U.S. PATENT DOCUMENTS

| | | | |
|---|---|---|---|
| 6,425,535 B1 * | 7/2002 | Akiba | 239/369 |
| 6,569,087 B2 | 5/2003 | Naito et al. | |
| 6,662,977 B2 * | 12/2003 | Gerber et al. | 222/494 |
| 7,278,553 B2 * | 10/2007 | Py et al. | 222/207 |
| 7,513,396 B2 * | 4/2009 | Pardes et al. | 222/494 |
| 7,757,711 B2 * | 7/2010 | Hama | 137/601.19 |
| 8,132,695 B2 * | 3/2012 | Py et al. | 222/207 |
| 8,550,308 B2 * | 10/2013 | Py et al. | 222/207 |
| 8,556,123 B2 * | 10/2013 | Py et al. | 222/83.5 |
| 2004/0112925 A1 * | 6/2004 | Py et al. | 222/494 |
| 2005/0072480 A1 * | 4/2005 | Brandes | 137/853 |
| 2007/0043262 A1 * | 2/2007 | Levy et al. | 600/156 |
| 2007/0244361 A1 * | 10/2007 | Ikeda et al. | 600/116 |
| 2008/0149191 A1 * | 6/2008 | Py et al. | 137/487.5 |

\* cited by examiner

CHECK VALVE ASSEMBLY FOR ENDOSCOPE

BACKGROUND OF THE INVENTION

1. Field of the Invention

The present invention relates to a check valve assembly for an endoscope. More particularly, the present invention relates to a check valve assembly for use between an endoscope and a fluid supply source, and in which a valve element can open and close reliably for preventing backflow even in a simple structure.

2. Description Related to the Prior Art

An endoscope includes an elongated tube or guide tube and a fluid lumen for water jet. The elongated tube is entered in a body cavity of a patient for imaging. The fluid lumen extends through the elongated tube, and used for ejecting fluid through a water jet nozzle at a distal end of the elongated tube. Examples of the fluid include drug solution for treatment, washing water such as physiological saline water, and the like. A fluid supply source or fluid dispensing apparatus is connected with the fluid lumen of the endoscope, and introduces the fluid by use of a supply pump. A check valve assembly for preventing backflow is used between the endoscope and the fluid supply source, and operates for preventing a backflow of the fluid from the fluid lumen back into the fluid supply source.

The fluid lumen of the endoscope has a distal end and a proximal end. The distal end has a water jet nozzle disposed at a distal surface of the elongated tube. The proximal end has a fluid port for water jet by connection with the check valve assembly. The fluid port is formed with a handle device of the endoscope on a proximal side of the elongated tube. Also, it is possible that the fluid port is formed with a connector disposed with the handle device for connection with a universal cable.

U.S. Pat. No. 6,569,087 (corresponding to JP-B 3488170) discloses an adapter tube set having first and second connection couplings at its ends. The first connection coupling is coupled to the fluid port of the endoscope. The second connection coupling is coupled to the fluid supply source. The check valve assembly is incorporated in the second connection coupling. The check valve assembly includes a discharge nozzle unit (or valve seat device) and an elastic valve sleeve (or elastic tubular portion or elastic check valve flap). The discharge nozzle unit has a cylindrical wall and plural fluid openings formed in the wall. The elastic valve sleeve covers the outside of the discharge nozzle unit. The elastic valve sleeve when in a normal state closes the fluid openings by tight contact with the outside of the discharge nozzle unit, and blocks supply of the fluid. When the fluid flows abruptly into the discharge nozzle unit, fluid pressure of the fluid from the fluid openings presses open the elastic valve sleeve to allow the fluid to flow into the fluid lumen. When the fluid pressure applied to the inside of the elastic valve sleeve decreases, return force of the elastic valve sleeve recovers its original form with the normal diameter. A backflow of the fluid can be prevented by closing of the fluid openings with the elastic valve sleeve.

The elastic valve sleeve constituting the check valve assembly has an inner diameter constant for the purpose of tight contact with the discharge nozzle unit in a normal state. Also, the elastic valve sleeve has a small diameter portion and a large diameter portion. The small diameter portion has a smaller diameter for a position to cover the fluid openings. The large diameter portion has a larger diameter than the small diameter portion. The large diameter portion is squeezed fixedly between the discharge nozzle unit and a valve housing in the axial direction, the discharge nozzle unit being mounted in the valve housing. Thus, the large diameter portion of the elastic valve sleeve with a larger thickness always contacts the discharge nozzle unit tightly. The small diameter portion with a smaller thickness is pressed open by the fluid pressure.

However, the elastic valve sleeve according to U.S. Pat. No. 6,569,087 (corresponding to JP-B 3488170) has a specific shape including the small diameter portion and the large diameter portion and must be formed only by use of particular molds or the like. This increases a manufacturing cost. It is conceivable to use a rubber tube of a commercially available type for the check valve assembly. If the check valve assembly is constituted by the rubber tube and the discharge nozzle unit of U.S. Pat. No. 6,569,087 (corresponding to JP-B 3488170), it is impossible exactly to position the check valve assembly for a position of the fluid openings typically when the return force of the rubber tube is too small.

If the rubber tube with a normally small diameter is used to increase return force in a state covering the discharge nozzle unit, the rubber tube tightly contacts the discharge nozzle unit with an equal level of the return force at any of its portions. The check valve assembly does not function, because a portion of the fluid openings cannot be controlled locally for opening and closing.

SUMMARY OF THE INVENTION

In view of the foregoing problems, an object of the present invention is to provide a check valve assembly for use between an endoscope and a fluid supply source, and in which a valve element can open and close reliably for preventing backflow even in a simple structure.

In order to achieve the above and other objects and advantages of this invention, a check valve assembly for connection between an endoscope and a fluid supply source is provided, and includes a discharge nozzle unit supplied with fluid by the fluid supply source, the discharge nozzle unit including a large diameter portion, a small diameter portion disposed on a distal side of the large diameter portion, a flow channel formed through the large diameter portion and partially through the small diameter portion, and a fluid opening, formed in an outer surface of the small diameter portion, for communicating with the flow channel. An elastic tubular portion is disposed around the outer surface of the small diameter portion and the large diameter portion, for preventing the fluid thereabout from passing outside the small diameter portion toward the fluid opening, and for allowing the fluid to flow out through a clearance space outside the small diameter portion upon being pushed open by the fluid from the fluid opening. A valve housing is connected with the endoscope, for containing the discharge nozzle unit with the elastic tubular portion, and for directing the fluid from the elastic tubular portion toward the endoscope.

The outer surface is inclined with an outer diameter decreasing from a position of the fluid opening toward a distal end of the small diameter portion in the discharge nozzle unit.

The small diameter portion includes an annular groove formed in the outer surface thereof in a circumferential direction and at the fluid opening.

The valve housing is cylindrical, and includes a positioning portion, formed on an inner surface thereof, fitted on the discharge nozzle unit, for positioning in an axial direction.

The positioning portion is an annular positioning ridge, and the discharge nozzle unit includes an annular groove engaged with the annular positioning ridge.

The positioning portion is an annular positioning groove, and the discharge nozzle unit includes an annular ridge engaged with the annular positioning groove.

The valve housing includes a packing portion for squeezing the elastic tubular portion in cooperation with the large diameter portion in a radial direction crosswise to the axial direction.

The packing portion is an annular packing projection.

The valve housing includes an engaging portion for rotationally regulating the discharge nozzle unit about an axis of the axial direction.

The engaging portion is an engaging cutout formed at a proximal end of the valve housing in the axial direction. The discharge nozzle unit includes a regulating projection engaged with the engaging cutout.

Furthermore, a flow channel is formed in the discharge nozzle unit to extend from an inner portion of the distal end to a proximal end of the discharge nozzle unit in the axial direction, for receiving the fluid at the proximal end, and drawing the fluid to the fluid opening. An inner diameter of the flow channel increases toward the proximal end.

The discharge nozzle unit includes a thread for helical engagement with a connection coupling of the fluid supply source.

The thread is male or female.

Furthermore, a flexible tube transfers the fluid from the valve housing to the endoscope.

Furthermore, a first connection coupling couples a first end of the flexible tube to the endoscope. A second connection coupling couples a second end of the flexible tube to the valve housing.

The elastic tubular portion is a tube of rubber or elastomer.

Accordingly, a valve element can open and close reliably for preventing backflow in a simple structure, because of the disposition of the fluid opening and the elastic tubular portion in the valve housing.

BRIEF DESCRIPTION OF THE DRAWINGS

The above objects and advantages of the present invention will become more apparent from the following detailed description when read in connection with the accompanying drawings, in which.

DETAILED DESCRIPTION OF THE PREFERRED EMBODIMENT(S) OF THE PRESENT INVENTION

Figure 1:
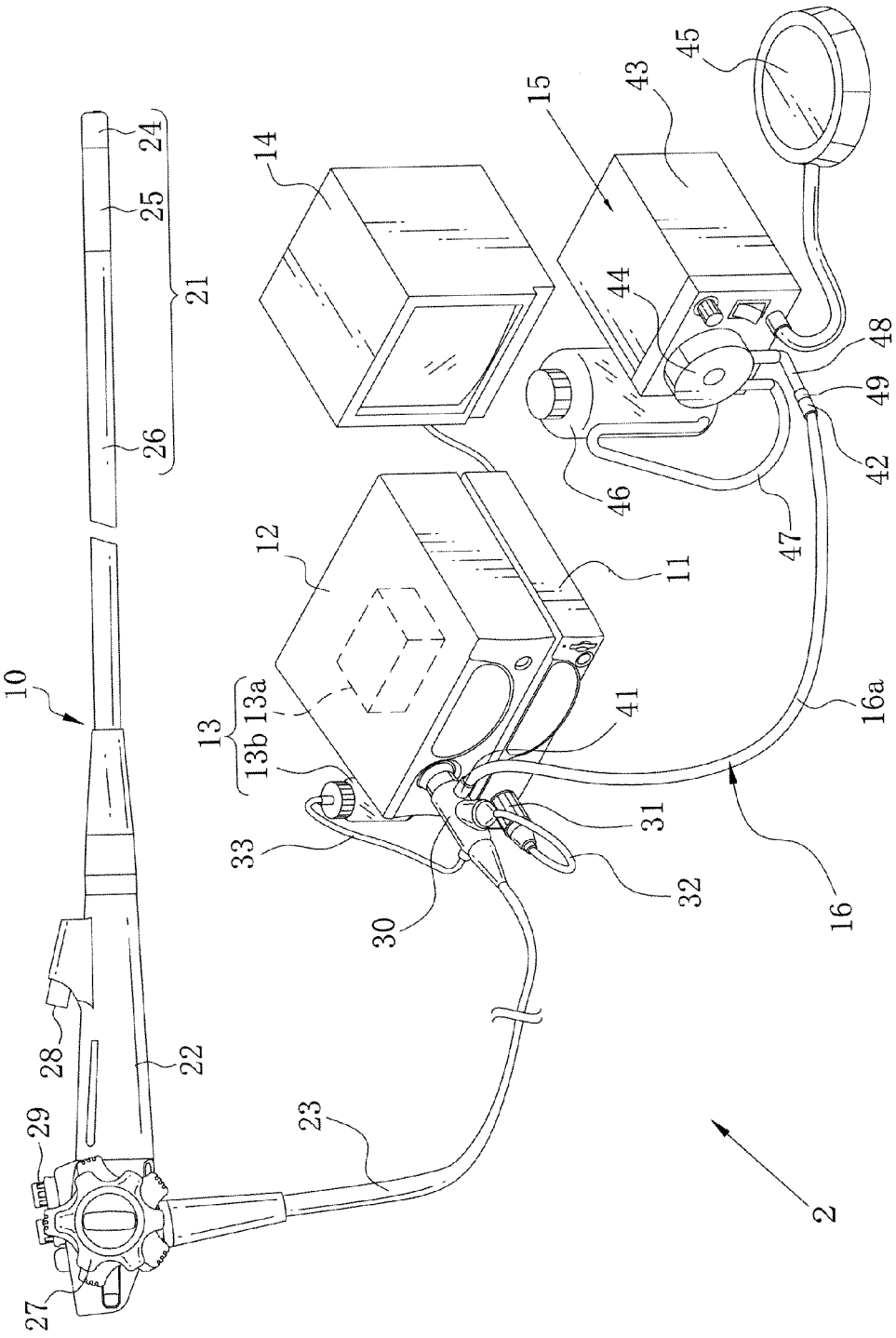
FIG. 1 is a perspective view illustrating an endoscope system.

In FIG. 1, an endoscope system 2 includes an endoscope 10, a processing apparatus 11, a light source apparatus 12, an air/water supply device 13, a monitor display panel 14, a fluid supply source 15 or fluid dispensing apparatus, and an adapter tube set 16. The air/water supply device 13 is incorporated in the light source apparatus 12, and includes an air pump 13a and a water reservoir 13b or tank. The air pump 13a is a well-known air supply source for supplying air. The water reservoir 13b is disposed outside the light source apparatus 12 and stores washing water.

The endoscope 10 includes an elongated tube 21 or guide tube, a handle device 22 and a universal cable 23. The elongated tube 21 is entered in a body cavity of a patient for imaging. The handle device 22 is disposed to extend from the elongated tube 21 in a proximal direction, and manipulated by a doctor or operator. The universal cable 23 extends from the handle device 22, and connects the endoscope 10 to external devices, such as the processing apparatus 11, the light source apparatus 12, the air/water supply device 13 and the fluid supply source 15.

The elongated tube 21 of the endoscope 10 includes a head assembly 24, a steering device 25 and a flexible tube device 26 as well-known in the art. The head assembly 24 includes a housing and an image pickup device. The housing of metal has sufficient rigidity. The image pickup device is contained in the housing.

An image processing device is incorporated in the processing apparatus 11, and processes an image signal from an image pickup device in the endoscope 10 for image processing of various functions, to create an endoscopic image. The image processing device encodes the endoscopic image with a composite signal and R, G and B component signals, which are output to the monitor display panel 14. The monitor display panel 14 is caused to display the endoscopic image.

Plural steering wheels 27 are disposed on the handle device 22, and operable for steering the steering device 25 up and down and to the right and left. This is effective in imaging a wall of a body cavity by the steering in any desired direction. The flexible tube device 26 is a portion of connection between the handle device 22 and the steering device 25, and has flexibility owing to its small diameter and long shape.

The handle device 22 includes a proximal instrument opening, an instrument channel 28, and an air/water supply button 29 as well as the steering wheels 27. The instrument opening is used for entry of a forceps or other medical instrument into the instrument channel 28. The air/water supply button 29 is manually operable for supplying air and water into the body cavity.

The universal cable 23 has a light guide connection plug 30 or LG connection plug and a video connection plug 31 at its end opposite to the handle device 22. The light guide connection plug 30 is used for connection with the light source apparatus 12. The video connection plug 31 is used for connection with the processing apparatus 11. A cable 32 is a line extending from the light guide connection plug 30 to the video connection plug 31. The endoscope 10 is connected to the light source apparatus 12 by the light guide connection plug 30 and to the processing apparatus 11 by the video connection plug 31 in a removable manner. The light guide connection plug 30 includes a first fluid port (not shown) for water supply and a fluid port 40 for water jet (See FIG. 3). A water input line 33 or tube extends from the first fluid port of the light guide connection plug 30 to the water reservoir 13b.

Figure 2:
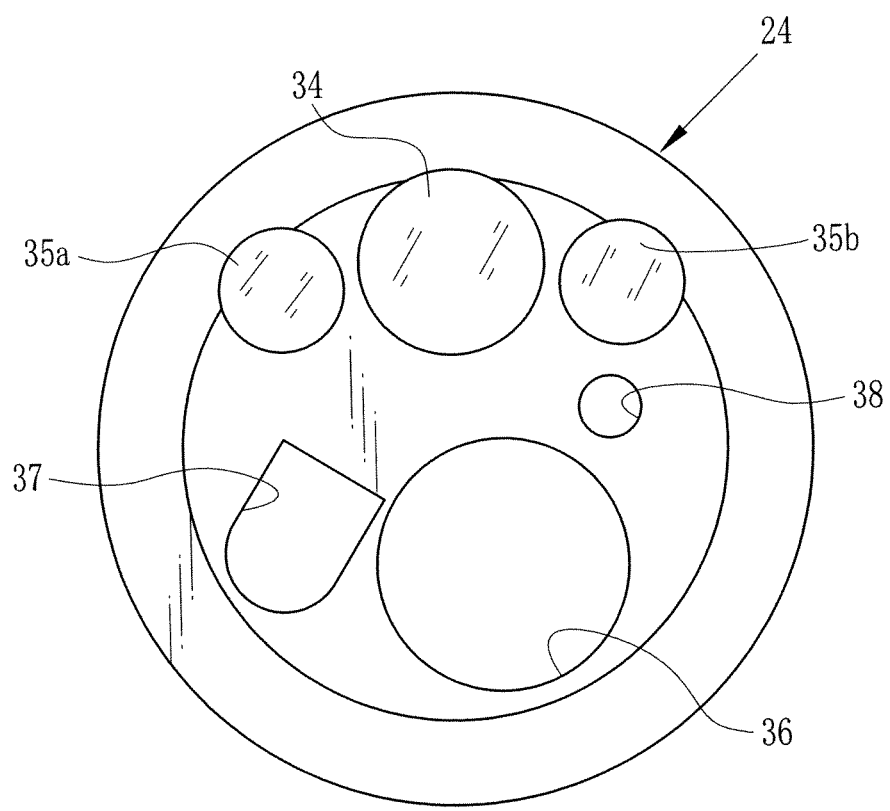
FIG. 2 is a front elevation illustrating a distal surface of a head assembly of an endoscope.

In FIG. 2, a distal surface of the head assembly 24 includes an imaging window 34, lighting windows 35a and 35b, an instrument opening 36, an air/water supply nozzle 37 and a water jet nozzle 38. The water jet nozzle 38 ejects any of various liquids to an object of interest in the body cavity, such as washing water, drug solution and the like. The image pickup device is disposed behind the imaging window 34. The lighting windows 35a and 35b are two arranged symmetrically with reference to the imaging window 34, and apply light from the light source apparatus 12 to the object of interest in the body cavity. The instrument opening 36 is open at a distal end of the instrument channel 28 formed to extend to the handle device 22. A forceps or other medical instrument is entered through the instrument channel 28, and emerges from the instrument opening 36 to project for medical treatment suitably. The air/water supply nozzle 37 ejects air or washing water from the air/water supply device 13 toward the imaging window 34, to wash away dust or dirt.

A fluid lumen 39 for water jet is formed to extend through the elongated tube 21, the handle device 22 and the universal cable 23. The water jet nozzle 38 is an end opening of the fluid lumen 39. See FIG. 3. The fluid lumen 39 is connected to the fluid supply source 15 to be described later. The water jet nozzle 38 extends in the axial direction of the imaging window 34, and ejects fluid directly to a wall of a body cavity when the fluid is supplied to the fluid lumen 39 from the fluid supply source 15. Also, the endoscope 10 includes an air supply channel and waste supply channel (not shown) for supplying air and washing water from the air/water supply device 13 to the air/water supply nozzle 37.

Figure 3:
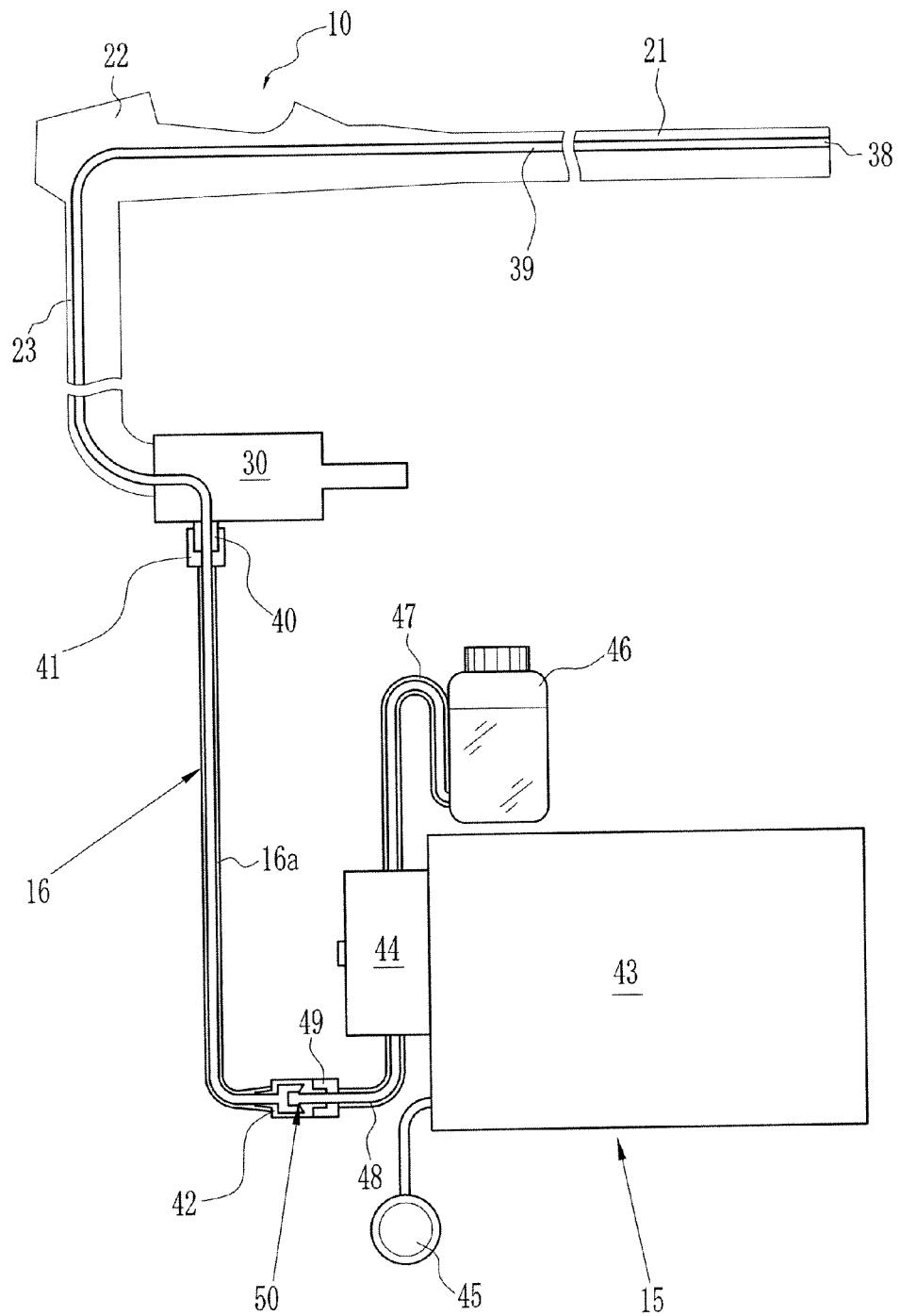
FIG. 3 is an explanatory view in a side elevation, illustrating the endoscope, a fluid supply source and an adapter tube set.

In FIG. 3, the fluid port 40 is disposed at an end of the fluid lumen 39 opposite to its end with the water jet nozzle 38. A wall of the fluid port 40 is formed integrally with an outer cover of the light guide connection plug 30. The fluid lumen 39 is connected to the fluid supply source 15 by the adapter tube set 16 which is attached to the fluid port 40.

In the embodiment, a check valve assembly 50 for preventing backflow is incorporated in the adapter tube set 16, which is used as a check valve apparatus for the endoscope. The adapter tube set 16 includes a flexible tube 16a, a first connection coupling 41 and a second connection coupling 42. The first connection coupling 41 is disposed at a distal end of the flexible tube 16a for connection of the fluid port 40 in a removable manner. The second connection coupling 42 is disposed at a proximal end of the flexible tube 16a for connection of the fluid supply source 15 in a removable manner.

The fluid supply source 15 includes a source housing 43, a fluid pump 44, a foot switch 45 and a fluid reservoir 46 or tank. The source housing 43 contains a motor, control circuit and other relevant elements. The fluid pump 44 is disposed in front of the source housing 43. The foot switch 45 is operable for supply of fluid. The fluid reservoir 46 stores washing water, drug solution and other fluids. A fluid input line 47 extends from the fluid reservoir 46 to the fluid pump 44 for flow of the fluid. A flow line 48 for supply extends from the fluid pump 44 for flow of the fluid. A connection coupling 49 is disposed at a distal end of the flow line 48 for connection with the second connection coupling 42 of the adapter tube set 16 in a removable manner.

Figure 4:
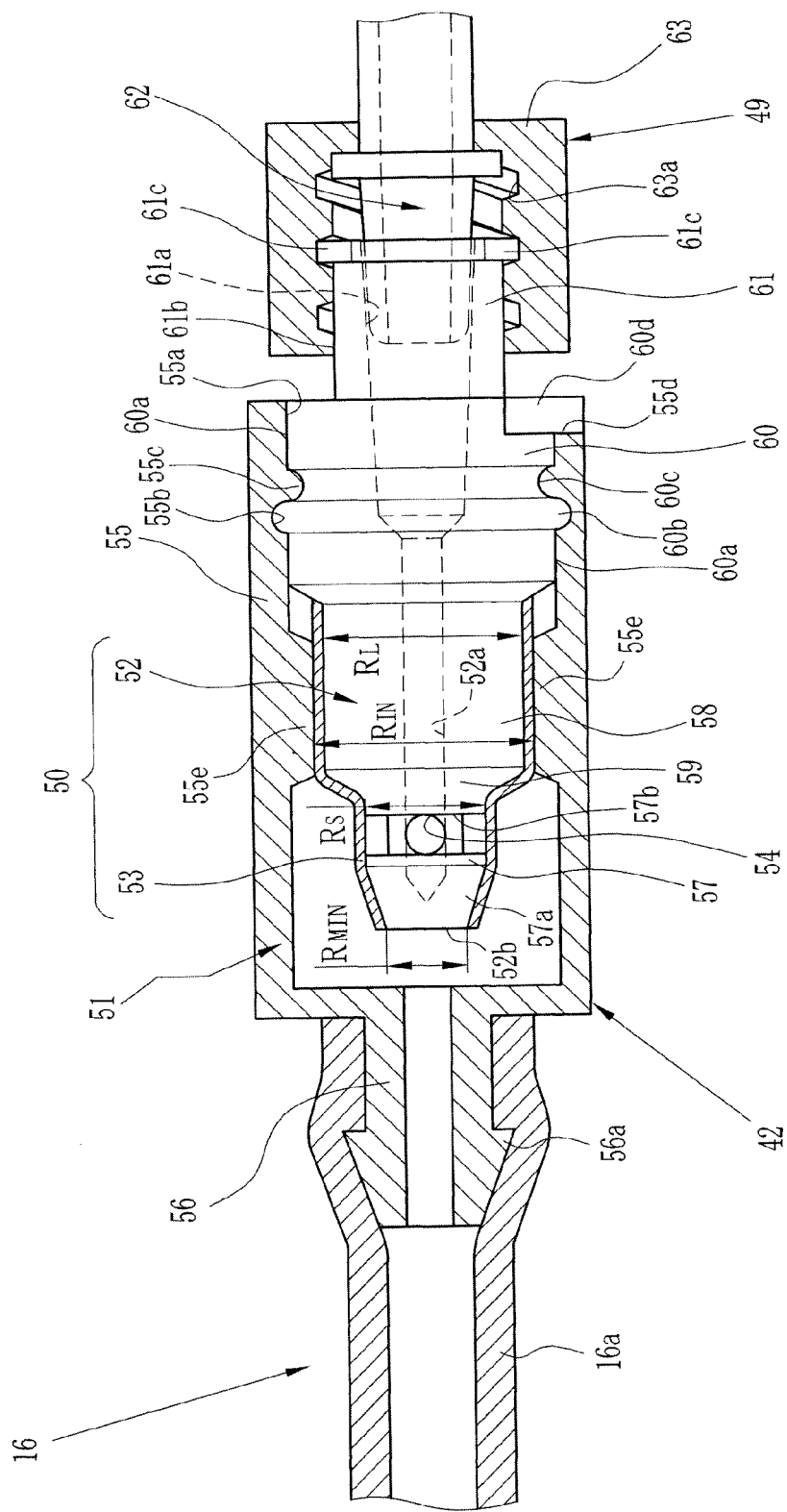
FIG. 4 is a vertical section illustrating a connection coupling with a check valve assembly.
Figure 5:
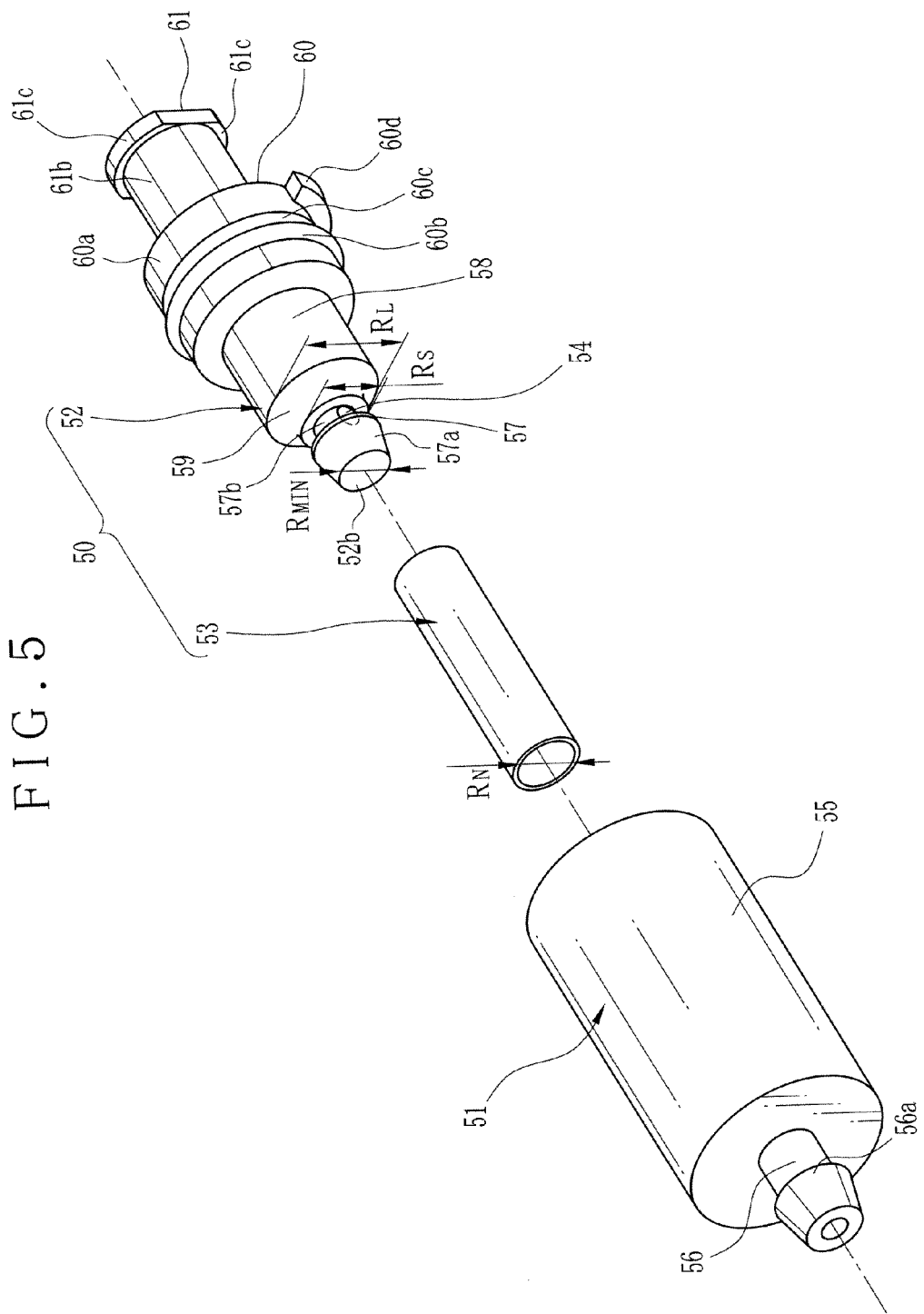
FIG. 5 is an exploded perspective view illustrating the connection coupling.
Figure 6:
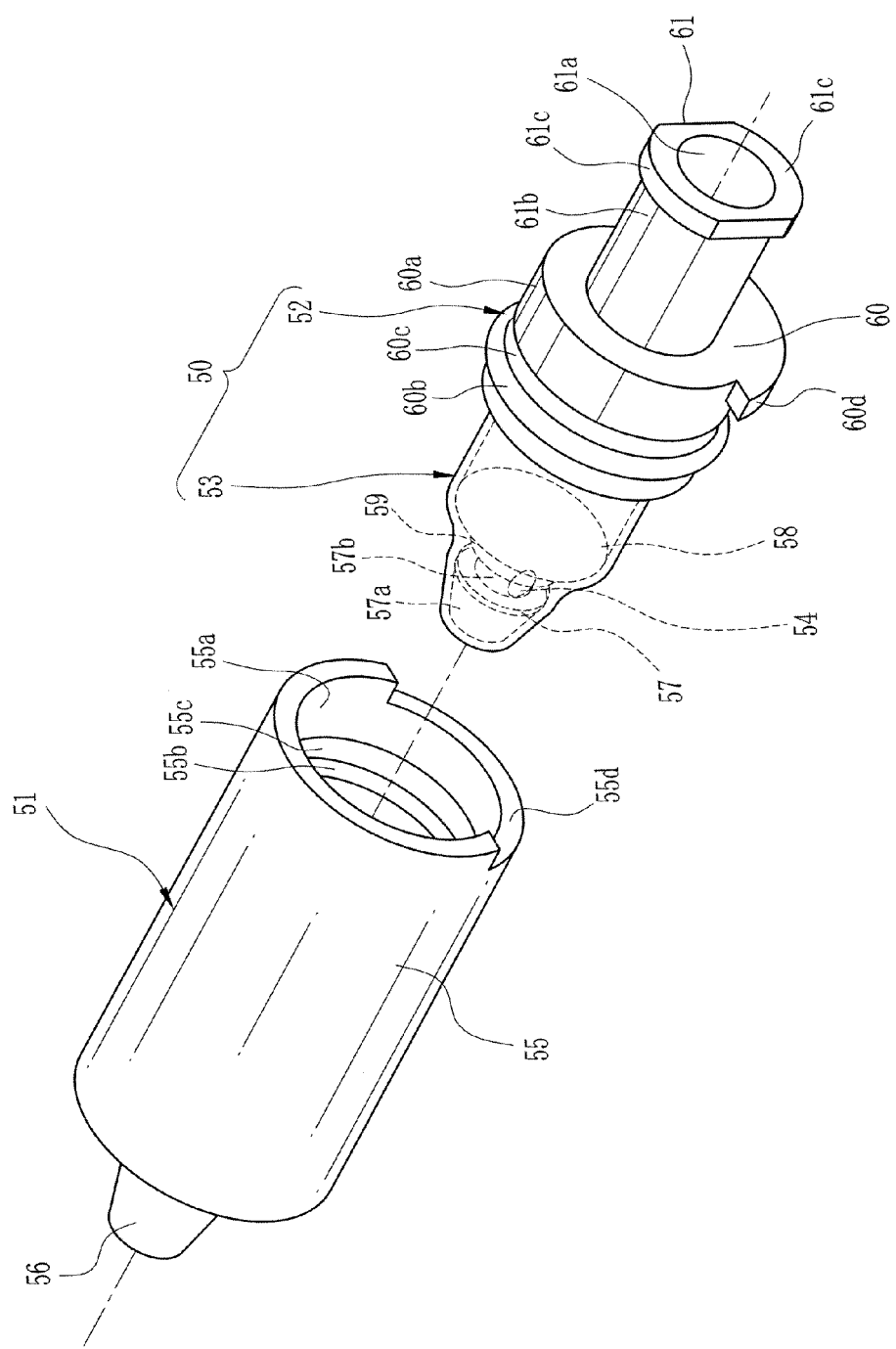
FIG. 6 is an exploded perspective view illustrating a discharge nozzle unit, a valve housing and an elastic tubular portion.

In FIGS. 4, 5 and 6, the second connection coupling 42 for the adapter tube set 16 includes a valve housing 51 or valve body and the check valve assembly 50. The check valve assembly 50 is contained in the valve housing 51, and prevents a backflow from the fluid lumen 39 to the fluid supply source 15.

The check valve assembly 50 includes a discharge nozzle unit 52 (or valve seat device) and an elastic tubular portion 53 (or elastic valve sleeve or elastic check valve flap). The discharge nozzle unit 52 has a closed distal end on a side of the endoscope 10. A fluid opening 54 is formed in the discharge nozzle unit 52 to come through its wall. The elastic tubular portion 53 covers the discharge nozzle unit 52 to close the fluid opening 54. The valve housing 51 includes a housing chamber 55 and a plug-in valve port 56 for coupling. The housing chamber 55 of a tubular shape contains the discharge nozzle unit 52 and the elastic tubular portion 53 together. The plug-in valve port 56 is disposed at a distal end of the housing chamber 55. An outer diameter of the portion of the plug-in valve port 56 is smaller than that of the housing chamber 55. An engaging flange 56a is formed at a distal end of the plug-in valve port 56. The outer portion of the plug-in valve port 56 is fitted on an inner surface of the flexible tube 16a. The engaging flange 56a is firmly engaged with the flexible tube 16a to fix the second connection coupling 42 on its tube end.

The discharge nozzle unit 52 includes a small diameter portion 57, a large diameter portion 58 and an intermediate portion 59. The small diameter portion 57 has the fluid opening 54. The large diameter portion 58 is positioned on a proximal side from the fluid opening 54, namely nearer to the fluid supply source 15. The intermediate portion 59 is disposed between the small and large diameter portions 57 and 58. An outer diameter RL of the large diameter portion 58 is larger than an outer diameter RS of the small diameter portion 57 in FIGS. 4 and 5. The intermediate portion 59 has an inclined surface extending smoothly between the small and large diameter portions 57 and 58. An outer surface of the large diameter portion 58 has a constant diameter in the axial direction.

The small diameter portion 57 includes a tapered outer surface 57a and an annular groove 57b. The tapered outer surface 57a is disposed at its distal end. The annular groove 57b is formed in its entire circumference. The discharge nozzle unit 52 has a distal end 52b. The tapered outer surface 57a has a diameter gradually decreasing from a position of the fluid opening 54 toward the distal end 52b. The annular groove 57b is formed in communication with the fluid opening 54, and is supplied with the fluid by the fluid opening 54.

To prepare the elastic tubular portion 53, a commercially available tube material of rubber or elastomer with a uniform thickness is used. The tube material is cut at a predetermined length in the axial direction to obtain the elastic tubular portion 53. Thus, it is possible to form the adapter tube set 16 at a low cost by utilizing the commercially available tube material.

An inner diameter RN (See FIG. 5) of the elastic tubular portion 53 in a normal state is smaller than the outer diameter RS of the small diameter portion 57, and is substantially equal to a minimum diameter RMIN (See FIGS. 4 and 5) of the tapered outer surface 57a. The elastic tubular portion 53 is fitted on the outside of the small diameter portion 57, the large diameter portion 58 and the intermediate portion 59 after enlarging the inner diameter RN for spreading. A proximal end portion of the elastic tubular portion 53 tightly contacts the discharge nozzle unit 52 because of an enlarged return force about the large diameter portion 58. A distal end portion of the elastic tubular portion 53 has such a smaller return force as to be pressed open by fluid pressure of fluid from the fluid opening 54. The elastic tubular portion 53 has the return force decreasing in the distal direction from the position of covering the fluid opening 54 because of the tapered outer surface 57a. Thus, a portion of the elastic tubular portion 53 nearer to the distal end from the fluid opening 54 can be pressed open more easily. Also, the annular groove 57b is formed in the entire circumference of the discharge nozzle unit 52. Fluid introduced in the annular groove 57b from the fluid opening 54 can press the elastic tubular portion 53 uniformly in the circumferential direction.

The discharge nozzle unit 52 includes a support sleeve 60 and a threaded sleeve 61. The support sleeve 60 is disposed on a proximal side from the large diameter portion 58. The threaded sleeve 61 is disposed on a proximal side from the support sleeve 60. The support sleeve 60 has a still larger outer diameter than the large diameter portion 58. The housing chamber 55 has an inner surface 55a. The support sleeve 60 is engaged with a proximal end of the inner surface 55a. The support sleeve 60 has an outer surface 60a. Adhesive agent is deposited between the outer surface 60a and the inner surface 55a of the housing chamber 55 and attaches the outer surface 60a to the inner surface 55a. Also, the support sleeve 60 has a ridge 60b and a groove 60c. The ridge 60b projects from the outer surface 60a annularly. The groove 60c is formed to retract annularly. The inner surface 55a of the housing chamber 55 includes a positioning groove 55b and a positioning ridge 55c. The positioning groove 55b is formed to receive the ridge 60b of the support sleeve 60. The positioning ridge 55c projects to enter the groove 60c. When the outer surface 60a of the support sleeve 60 is engaged with the inner surface 55a of the housing chamber 55, the ridge 60b and the groove 60c are retained on respectively the positioning groove 55b and the positioning ridge 55c, so as to position the support sleeve 60 relative to the housing chamber 55 exactly in the axial direction. Thus, the discharge nozzle unit 52 is fixedly mounted in the valve housing 51. Note that the positioning ridge 55c of the housing chamber 55 may have no continuous form in the inner surface 55a. For example, the positioning ridge 55c can be constituted by a plurality of positioning projections of a short shape arranged circumferentially at an equal pitch.

A regulating projection 60d is formed at a proximal end of the support sleeve 60 to project locally from the outer surface 60a. An engaging cutout 55d as engaging portion for regulation is formed at a proximal end of the housing chamber 55, and is disposed at the regulating projection 60d in the circumference. When the outer surface 60a of the support sleeve 60 is engaged with the inner surface 55a of the housing chamber 55, the discharge nozzle unit 52 is regulated rotationally about the axis relative to the valve housing 51 as the regulating projection 60d is entered in the engaging cutout 55d.

An annular packing projection 55e or flange is formed to project from the inner surface 55a of the housing chamber 55 toward the axis in the radial direction in the valve housing 51. The annular packing projection 55e is disposed for coming at the large diameter portion 58 of the discharge nozzle unit 52 upon engaging the outer surface 60a of the support sleeve 60 with the inner surface 55a of the housing chamber 55 and retaining the ridge 60b and the groove 60c on the positioning groove 55b and the positioning ridge 55c. The outer diameter RL of the large diameter portion 58 is larger than an inner diameter RIN of the annular packing projection 55e when the large diameter portion 58 is covered with the elastic tubular portion 53. When the discharge nozzle unit 52 is mounted fixedly in the valve housing 51 together with the elastic tubular portion 53 for covering, the elastic tubular portion 53 is squeezed between the annular packing projection 55e and the large diameter portion 58 in the radial direction.

As illustrated in FIG. 4, a Leur lock mechanism is constituted by the threaded sleeve 61 of the discharge nozzle unit 52 with the connection coupling 49 of the fluid supply source 15. The discharge nozzle unit 52 has a flow channel 52a. An inclined surface 61a is defined inside the threaded sleeve 61, is a proximal part of the flow channel 52a, and has a decreasing diameter in a distal direction. An outer surface 61b of the threaded sleeve 61 has a male thread 61c constructed helically. In the embodiment, the male thread 61c has two projections. The connection coupling 49 includes a nozzle 62 and a coupling housing 63. The nozzle 62 is a fluid port and has a tapered wall corresponding to the inclined surface 61a of the threaded sleeve 61. The coupling housing 63 is fitted on the outside of the nozzle 62. A female thread 63a is formed inside the coupling housing 63 helically. The nozzle 62 is provided at an end of the flow line 48 of the fluid supply source 15. For the connection coupling 49 and the threaded sleeve 61, the coupling housing 63 is rotated while the nozzle 62 is moved in and fitted on the inclined surface 61a. The female thread 63a is helically engaged with the male thread 61c to couple the connection coupling 49 with the threaded sleeve 61 removably. Then the second connection coupling 42 is connected with the connection coupling 49. The flow line 48 comes to communicate with the discharge nozzle unit 52 through the nozzle 62, to supply fluid from the fluid supply source 15 into the flow channel 52a.

The operation of the above-described construction is described now, specially for ejection of fluid from the fluid lumen 39 of the endoscope 10 through the water jet nozzle 38. At first, the first connection coupling 41 of the adapter tube set 16 is coupled to the fluid port 40 of the endoscope 10. The second connection coupling 42 is coupled to the connection coupling 49 of the fluid supply source 15. A power source for the fluid supply source 15 is turned on to operate the fluid pump 44 by depressing the foot switch 45. Fluid is drawn by the flow line 48 to the fluid lumen 39 through the connection coupling 49, the second connection coupling 42, the flexible tube 16a, the first connection coupling 41 and the fluid port 40. The water jet nozzle 38 ejects the fluid.

Figure 7:
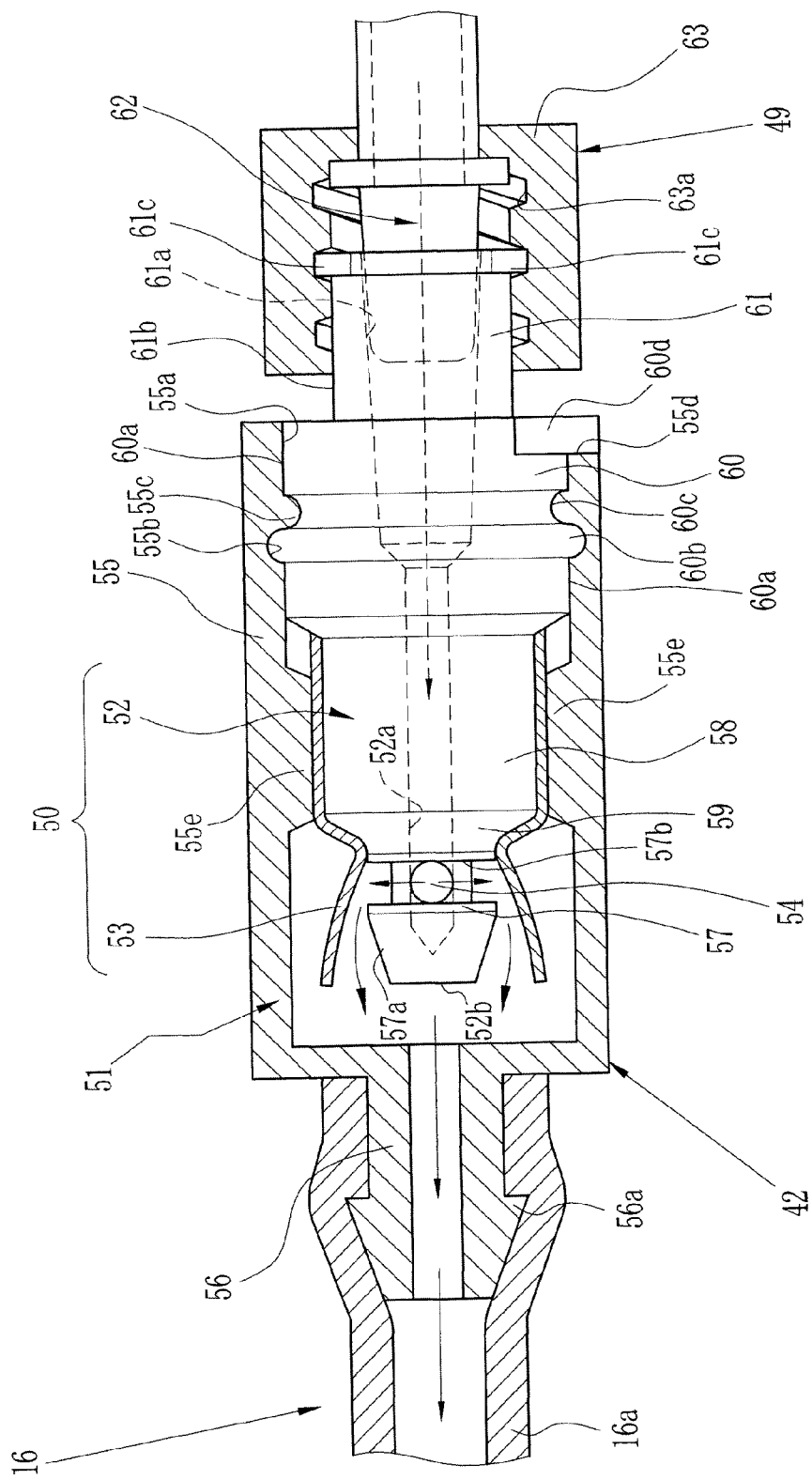
FIG. 7 is a vertical section illustrating a state of supply of fluid into the connection coupling.

When the fluid from the flow line 48 of the fluid supply source 15 flows into the flow channel 52a of the discharge nozzle unit 52 as illustrated in FIG. 7, the fluid flows through the fluid opening 54 and presses the inside of the elastic tubular portion 53. While the proximal end portion of the elastic tubular portion 53 remains in tight contact with the large diameter portion 58, its distal end portion is pressed open. As the annular groove 57b is formed in the entire circumference, the distal portion of the elastic tubular portion 53 is opened nearly uniformly in the circumferential direction. Therefore, the fluid can flow smoothly, as the elastic tubular portion 53 extends nearly in parallel with the flow direction of the fluid in the open state of the distal end portion in contrast with the proximal end portion of the elastic tubular portion 53.

The supply of the fluid from the fluid supply source 15 is stopped when the depression of the foot switch 45 is discontinued. As the fluid pressure of the inside of the elastic tubular portion 53 decreases, the distal end of the elastic tubular portion 53 is caused tightly to contact the small diameter portion 57 by its return force, to close the fluid opening 54. See the state of FIG. 4. It is possible to prevent a backflow of the fluid from the endoscope 10 to the fluid supply source 15 as the check valve assembly 50 opens and closes reliably.

The annular groove 57b is formed in the entire circumference of the small diameter portion 57. For cleaning the adapter tube set 16, washing water is drawn through a proximal end of the discharge nozzle unit 52 into the flow channel 52a to press open the elastic tubular portion 53 at a predetermined clearance space in the circumferential direction. This is effective in smoothing the flow of the washing water or cleaning fluid even with a high viscosity. Cleanability of the adapter tube set 16 can be high.

The second connection coupling 42 must be rotated about the axis for engaging or disengaging the male thread 61c relative to the female thread 63a for the purpose of connecting or disconnecting the adapter tube set 16 with the fluid supply source 15. However, no screws are used for coupling parts of the second connection coupling 42. Thus, it is possible to keep the parts coupled to one another in the second connection coupling 42. In short, the outer surface 60a of the support sleeve 60 is fitted in the inner surface 55a of the housing chamber 55. The ridge 60b and the groove 60c are retained on the positioning groove 55b and the positioning ridge 55c. The regulating projection 60d is engaged with the engaging cutout 55d to regulate rotation of the discharge nozzle unit 52 relative to the valve housing 51 about the axis. Thus, the discharge nozzle unit 52 can be kept contained in the valve housing 51. Drop of adhesive agent between those can be prevented.

Also, the elastic tubular portion 53 is squeezed in the radial direction by the large diameter portion 58 and the annular packing projection 55e, so that return force for pressing the discharge nozzle unit 52 and the valve housing 51 occurs in the radial direction. In contrast, the discharge nozzle unit 52 tightly contacts the valve housing 51 owing to the entry in the axial direction. The direction of the push of the elastic tubular portion 53 to the discharge nozzle unit 52 and the valve housing 51 is perpendicular to the direction of the entry of the discharge nozzle unit 52 in the valve housing 51. The tight contact of the discharge nozzle unit 52 in the valve housing 51 can remain without separation even upon occurrence of the return force of the elastic tubular portion 53. Furthermore, the discharge nozzle unit 52 is mounted fixedly in the valve housing 51 as described above. The elastic tubular portion 53 is always squeezed between the large diameter portion 58 and the annular packing projection 55e and kept in a predetermined position, and can be maintained in contact with the discharge nozzle unit 52 without drop. Specially if a flow rate of the fluid from the fluid supply source 15 is large, the check valve assembly 50 can open and close reliably, because the elastic tubular portion 53 is firmly held on the discharge nozzle unit 52. Note that a check valve assembly according to the conventional technique has the elastic tubular portion squeezed in the axial direction. This causes a problem in that its parts are likely to move away in the axial direction due to occurrence of return force to press the parts in the axial direction. However, such a problem is resolved in the present invention.

Figure 8:
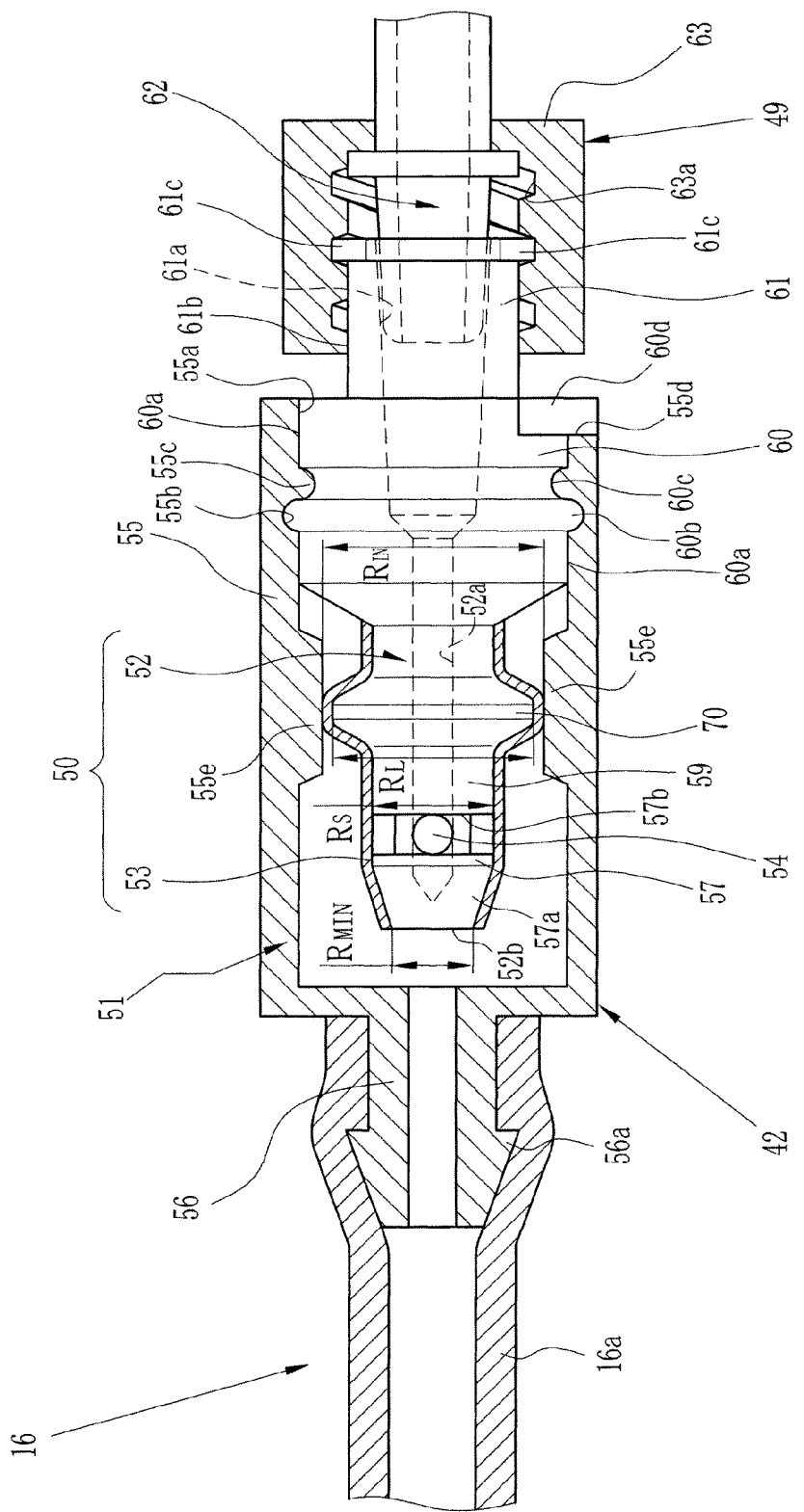
FIG. 8 is a vertical section illustrating another preferred embodiment of check valve assembly.

In the above embodiment, the large diameter portion 58 of the discharge nozzle unit 52 has a wide cylindrical shape with a constant diameter. In contrast, FIG. 8 illustrates another preferred large diameter portion 70 formed to project from the small diameter portion 57 in a relatively narrow shape. The large diameter portion 70 is disposed on a proximal side from the fluid opening 54. The outer diameter RL of a highest position of the large diameter portion 70 is larger than the inner diameter FIN of the annular packing projection 55e in the course of covering the large diameter portion 70 with the elastic tubular portion 53. This makes it possible to obtain the same effects. The elastic tubular portion 53 is squeezed in the radial direction between the large diameter portion 70 and the annular packing projection 55e in the manner of the above embodiment. The elastic tubular portion 53 can be maintained reliably in the predetermined position, and kept on the discharge nozzle unit 52 without drop.

Furthermore, the small diameter portion 57 in the discharge nozzle unit 52 of FIG. 8 can be a head portion of which the outer diameter RS may be not smaller than the outer diameter RL. The structure of this head portion is effective in facilitating pushing open of the elastic tubular portion 53 because the fluid pressure at the head portion can be kept high without drop.

In the above embodiment, an inner diameter of the flow channel 52a is constant in a range between the small and large diameter portions 57 and 58, and substantially equal to a width of the fluid opening 54. However, the inner diameter of the flow channel 52a can be increased or decreased in a conical form or the like, and may be different from the width of the fluid opening 54.

In the above embodiments, the adapter tube set 16 as a check valve assembly is connected with the fluid port 40 provided in the light guide connection plug 30. However, it is possible in the invention to connect a check valve assembly with a fluid port provided in a handle device of the endoscope.

In the above embodiment, the check valve assembly is incorporated in the second connection coupling of the adapter tube set near to the fluid supply source and not in the first connection coupling near to the endoscope. However, a check valve assembly of the invention can be incorporated in the first connection coupling. In the above embodiment, the adapter tube set has the check valve assembly of the invention. However, an intermediate adapter can be connected between a fluid port of the endoscope and the second connection coupling near to the fluid supply source, and can include a check valve assembly of the present invention.

In the above embodiment, the female thread is formed with the connection coupling of the fluid supply source and the male thread is formed with the connection coupling of the discharge nozzle unit. In contrast, a male thread can be formed with the connection coupling of the fluid supply source. A female thread can be formed with the connection coupling of the discharge nozzle unit.

Note that the fluid supply source, although an automatically operating device according to the embodiment, may be a syringe pump and other devices operable manually. Fluid for supply to the endoscope through the check valve assembly may be gas, such as air, anesthetic agent of a gaseous phase, and the like.

In the above embodiments, the image pickup device or image sensor is used in the endoscope. Also, an endoscope according to the invention can include an optical image guide for imaging.

Although the present invention has been fully described by way of the preferred embodiments thereof with reference to the accompanying drawings, various changes and modifications will be apparent to those having skill in this field. Therefore, unless otherwise these changes and modifications depart from the scope of the present invention, they should be construed as included therein.

What is claimed is:

1. A check valve assembly connected between an endoscope and a fluid supply source, comprising:
   a discharge nozzle unit supplied with fluid by said fluid supply source, said discharge nozzle unit including a large diameter portion, a small diameter portion disposed on a distal side of said large diameter portion, a flow channel formed through said large diameter portion and partially through said small diameter portion, and a fluid opening, formed in an outer surface of said small diameter portion, for communicating with said flow channel;
   an elastic tubular portion, disposed around said outer surface of said small diameter portion and said large diameter portion, for preventing said fluid thereabout from passing outside said small diameter portion toward said fluid opening, and for allowing said fluid to flow out through a clearance space outside said small diameter portion upon being pushed open by said fluid from said fluid opening; and
   a valve housing, connected with said endoscope, for containing said discharge nozzle unit with said elastic tubular portion, and for directing said fluid from said elastic tubular portion toward said endoscope, wherein said valve housing includes an engaging portion for rotationally regulating said discharge nozzle unit about an axis of an axial direction, wherein said engaging portion includes an engaging cutout formed at a proximal end of said valve housing in said axial direction, and wherein said discharge nozzle unit includes a regulating projection engaged with said engaging cutout.

2. A check valve assembly as defined in claim 1, wherein said outer surface is inclined with an outer diameter decreasing from a position of said fluid opening toward a distal end of said small diameter portion in said discharge nozzle unit.

3. A check valve assembly as defined in claim 2, wherein said small diameter portion includes an annular groove formed in said outer surface thereof in a circumferential direction and at said fluid opening.

4. A check valve assembly as defined in claim 2, wherein said elastic tubular portion comprises a tube of rubber or elastomer.

5. A check valve assembly as defined in claim 2, further comprising a flexible tube for connecting said valve housing to said endoscope.

6. A check valve assembly as defined in claim 5, further comprising:
a first connection coupling for coupling a first end of said flexible tube to said endoscope;
a second connection coupling for coupling a second end of said flexible tube to said valve housing.

7. A check valve assembly as defined in claim 2, wherein said valve housing is cylindrical, and includes a positioning portion, formed on an inner surface thereof, fitted on said discharge nozzle unit, for positioning in said axial direction.

8. A check valve assembly as defined in claim 7, wherein said positioning portion comprises an annular positioning ridge, and said discharge nozzle unit includes an annular groove engaged with said annular positioning ridge.

9. A check valve assembly as defined in claim 7, wherein said positioning portion comprises an annular positioning groove, and said discharge nozzle unit includes an annular ridge engaged with said annular positioning groove.

10. A check valve assembly as defined in claim 7, wherein an inner diameter of said flow channel at a proximal end thereof is larger than an inner diameter of said flow channel at a distal end thereof.

11. A check valve assembly as defined in claim 7, wherein said discharge nozzle unit includes a thread, disposed on a proximal side, for helical engagement with a connection coupling of said fluid supply source.

12. A check valve assembly as defined in claim 7, wherein said valve housing includes a packing portion for squeezing said elastic tubular portion in cooperation with said large diameter portion in a radial direction crosswise to said axial direction.

13. A check valve assembly as defined in claim 12, wherein said packing portion comprises an annular packing projection.

14. A check valve assembly connected between an endoscope and a fluid supply source, comprising:
a discharge nozzle unit supplied with fluid by said fluid supply source, said discharge nozzle unit including a large diameter portion, a head portion disposed on a distal side of said large diameter portion, a flow channel formed through said large diameter portion and partially through said head portion, and a fluid opening, formed in an outer surface of said head portion, for communicating with said flow channel;
an elastic tubular portion, disposed around said outer surface of said head portion and said large diameter portion, for preventing said fluid thereabout from passing outside said head portion toward said fluid opening, and for allowing said fluid to flow out through a clearance space outside said head portion upon being pushed open by said fluid from said fluid opening; and
a valve housing, connected with said endoscope, for containing said discharge nozzle unit with said elastic tubular portion, and for directing said fluid from said elastic tubular portion toward said endoscope,
wherein said valve housing includes an engaging portion for rotationally regulating said discharge nozzle unit about an axis of an axial direction,
wherein said engaging portion includes an engaging cutout formed at a proximal end of said valve housing in said axial direction, and
wherein said discharge nozzle unit includes a regulating projection engaged with said engaging cutout.

* * * * *